United States Patent
Perkins et al.

(10) Patent No.: US 10,188,500 B2
(45) Date of Patent: Jan. 29, 2019

(54) STENT GRAFT WITH EXTERNAL SCAFFOLDING AND METHOD

(71) Applicant: Medtronic Vascular, Inc., Santa Rosa, CA (US)

(72) Inventors: Keith Perkins, Santa Rosa, CA (US); Jeffery Argentine, Petaluma, CA (US); Matt Petruska, Windsor, CA (US); Samuel Robaina, Novato, CA (US); Darren Galligan, San Francisco, CA (US); Rajesh Radhakrishnan, Petaluma, CA (US)

(73) Assignee: Medtronic Vascular, Inc., Minneapolis, MN (US)

( * ) Notice: Subject to any disclaimer, the term of this patent is extended or adjusted under 35 U.S.C. 154(b) by 40 days.

(21) Appl. No.: 15/043,246

(22) Filed: Feb. 12, 2016

(65) Prior Publication Data
US 2017/0231749 A1    Aug. 17, 2017

(51) Int. Cl.
*A61F 2/06* (2013.01)
*A61F 2/07* (2013.01)
*A61F 2/00* (2006.01)

(52) U.S. Cl.
CPC ............. *A61F 2/07* (2013.01); *A61F 2/0077* (2013.01); *A61F 2002/065* (2013.01); *A61F 2002/068* (2013.01); *A61F 2002/075* (2013.01); *A61F 2002/077* (2013.01); *A61F 2210/0061* (2013.01); *A61F 2230/0065* (2013.01); *A61F 2250/0051* (2013.01); *A61F 2250/0056* (2013.01); *A61F 2310/00023* (2013.01)

(58) Field of Classification Search
CPC ................. A61F 2/07; A61F 2002/077; A61F 2230/0065; A61F 2250/003; A61F 2002/068
See application file for complete search history.

(56) References Cited

U.S. PATENT DOCUMENTS

| | | |
|---|---|---|
| 5,693,088 A | 12/1997 | Lazarus |
| 2003/0074055 A1 | 4/2003 | Haverkost |
| 2004/0204755 A1* | 10/2004 | Robin ................. A61F 2/07 623/1.21 |
| 2009/0138070 A1* | 5/2009 | Holzer ................ A61F 2/07 623/1.15 |
| 2014/0058436 A1 | 2/2014 | Rosenbluth |
| 2016/0030155 A1 | 2/2016 | Cox et al. |

OTHER PUBLICATIONS

PCT/US2017/017327, The International Search Report and the Written Opinion of the International Searching Authority, dated Mar. 29, 2017, 14pgs.

(Continued)

*Primary Examiner* — Brian Dukert (57) ABSTRACT

A scaffolded stent-graft includes a graft material comprising an inner surface and an outer surface. The inner surface defines a lumen within the graft material. The scaffolded stent-graft further includes a scaffold comprising a mesh coupled to the graft material at the outer surface. The scaffold is configured to promote tissue ingrowth therein. In this manner, the scaffold enhances tissue integration into the scaffolded stent-graft. The tissue integration enhances biological fixation of the scaffolded stent-graft in vessels minimizing the possibility of endoleaks and migration.

18 Claims, 6 Drawing Sheets

(56) References Cited

OTHER PUBLICATIONS

Szilagyi, D. Emerick "The Problem of Healing of Endovascular Stent Grafts in the Repair of Abdominal Aortic Aneurysms" Journal of Vascular Surgery, Jun. 2001, pp. 1283-1285.
Berger et al. "Healing of Arterial Prostheses in Man: It's Incompleteness" Ann. Surg. Jan. 1972, vol. 175, No. 1.
Major et al. "Implant Degradation and Poor Healing After Endovascular Repair of Abdominal Aortic Aneurysms" J Endovasc Ther 2006; 13:457-467.
Malina et al. "Endovascular Healing is Inadequate for Fixation of Dacron Stent-Grafts in Human Aortoiliac Vessels" Uer J Vasc Endovasc Surg 19, 5-11 (2000).
McArthur et al. "Histopathologic Analysis of Endovascular Stent Grafts From Patients With Aortic Aneurysms: Does Healing Occur?" Journal of Vascular Surgery, Apr. 2001 pp. 733-738.
Pasquinelli et al., "Healing of Prosthetic Arterial Grafts" Scanning Microscopy, vol. 4, No. 2, 1990 (pp. 351-362).
Zilla et al., "Prosthetic Vascular Grafts: Wrong Models, Wrong Questions and No Healing" Biomaterials 28 (2007) 5009-5027.

* cited by examiner

STENT GRAFT WITH EXTERNAL SCAFFOLDING AND METHOD

BACKGROUND

Field

The present application relates to an intra-vascular device and method. More particularly, the present application relates to a device for treatment of intra-vascular diseases.

Description of the Related Art

A conventional stent-graft typically includes a radially expandable reinforcement structure, formed from a plurality of annular stent rings, and a cylindrically shaped layer of graft material defining a lumen to which the stent rings are coupled. Stent-grafts are well known for use in tubular shaped human vessels.

To illustrate, endovascular aneurysmal exclusion is a method of using a stent-graft to exclude pressurized fluid flow from the interior of an aneurysm, thereby reducing the risk of rupture of the aneurysm and the associated invasive surgical intervention.

The graft material of traditional stent-grafts is extremely hydrophobic and presents a hostile environment for the recruitment and proliferation of cells. The inability of tissue to integrate into the graft material prevents the biological fixation of the stent-graft in vessels and makes the stent-graft susceptible to endoleaks and migration.

SUMMARY

In accordance with one embodiment, a scaffolded stent-graft includes a graft material comprising an inner surface and an outer surface. The inner surface defines a lumen within the graft material. The scaffolded stent-graft further includes a scaffold comprising a mesh coupled to the graft material at the outer surface.

The scaffold is configured to promote tissue ingrowth therein. In this manner, the scaffold enhances tissue integration into the scaffolded stent-graft. The tissue integration enhances biological fixation of the scaffolded stent-graft in vessels minimizing the possibility of endoleaks and migration.

BRIEF DESCRIPTION OF DRAWINGS

Common reference numerals are used throughout the drawings and detailed description to indicate like elements.

DETAILED DESCRIPTION

As an overview and in accordance with one embodiment, a scaffolded stent-graft includes a graft material and an external scaffold. The graft material provides a barrier to tissue integration. The external scaffold is more suited to promote tissue integration and is mechanically attached to the graft material. Tissue incorporation into the external scaffold creates a biological fixation with the native vessel, thus minimizing the possibility of endoleaks and migration.

Figure 1:
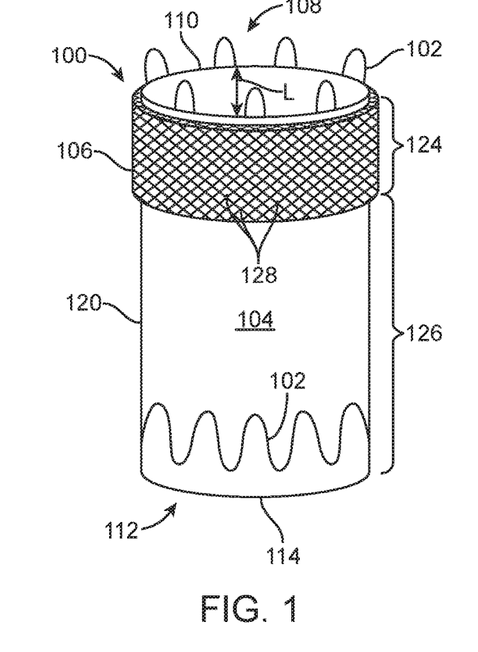
FIG. 1 is a perspective view of a scaffolded stent-graft in accordance with one embodiment.

More particularly, FIG. 1 is a perspective view of a scaffolded stent-graft 100, e.g., an abdominal aortic stent-graft, in accordance with one embodiment. Referring now to FIG. 1, scaffolded stent-graft 100 includes one or more stent rings 102. Illustratively, stent rings 102 are self-expanding stent rings, e.g., nickel titanium alloy (NiTi), sometimes called Nitinol. The inclusion of stent rings 102 is optional and in one embodiment stent rings 102 are not included.

Figure 2:
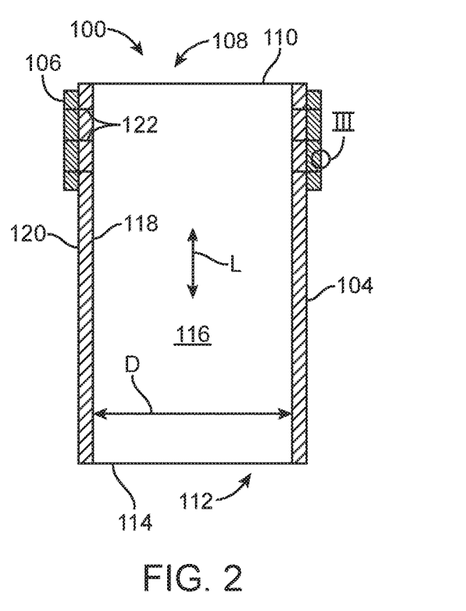
FIG. 2 is a cross-sectional view of the scaffolded stent-graft of FIG. 1 in accordance with one embodiment.

FIG. 2 is a cross-sectional view of scaffolded stent-graft 100 of FIG. 1 in accordance with one embodiment. In FIG. 2, stent rings 102 are not illustrated for clarity of presentation.

Referring now to FIGS. 1 and 2 together, scaffolded stent-graft 100 includes a graft material 104 and a scaffold 106. In accordance with this embodiment, graft material 104 includes a proximal opening 108 at a proximal end 110 of graft material 104 and a distal opening 112 at a distal end 114 of graft material 104.

Further, scaffolded stent-graft 100 includes a longitudinal axis L. A lumen 116 is defined by graft material 104, and generally by scaffolded stent-graft 100. Lumen 116 extends generally parallel to longitudinal axis L and between proximal opening 108 and distal opening 112 of scaffolded stent-graft 100.

As used herein, the proximal end of a prosthesis such as a stent-graft is the end closest to the heart via the path of blood flow whereas the distal end is the end furthest away from the heart during deployment. In contrast and of note, the distal end of the catheter is usually identified to the end that is farthest from the operator (handle) while the proximal end of the catheter is the end nearest the operator (handle).

For purposes of clarity of discussion, as used herein, the distal end of the catheter is the end that is farthest from the operator (the end furthest from the handle) while the distal end of the prosthesis is the end nearest the operator (the end nearest the handle), i.e., the distal end of the catheter and the proximal end of the stent-graft are the ends furthest from the handle while the proximal end of the catheter and the distal end of the stent-graft are the ends nearest the handle. However, those of skill in the art will understand that depending upon the access location, the stent-graft and delivery system description may be consistent or opposite in actual usage.

Graft material 104 is cylindrical having a substantially uniform diameter D. However, in other embodiments, graft material 104 varies in diameter and/or is bifurcated at distal end 114. Graft material 104 includes a cylindrical inner surface 118 and an opposite outer surface 120.

In one embodiment, graft material 104 is hydrophobic, e.g., is polyester terephthalate (PET), expanded polyester terephthalate (ePET), or other graft material. As graft material 104 is hydrophobic, graft material 104 presents a hostile environment for the recruitment and the proliferation of cells.

In one embodiment, to enhance tissue integration, scaffold 106 is attached to outer surface 120 of graft material 104 by an attachment means 122. Illustratively, attachment means 122 is stitching, adhesive, thermal bonding, or other attachment between scaffold 106 and graft material 104.

In accordance with this embodiment, scaffold 106 is attached to graft material 104 at or adjacent proximal end 110 of graft material 104. The region 124 of graft material 104 which is covered by scaffold 106 is referred to as a seal zone 124 of graft material 104. The region 126 of graft material 104 which is uncovered by scaffold 106 is referred to as a bare zone 126 of graft material 104. Seal zone 124 extends distally from proximal end 110 to bare zone 126. Bare zone 126 extends distally from seal zone 124 to distal end 114.

In accordance with this embodiment, scaffold 106 is a mesh. In one embodiment, a mesh is an interlaced or solid structure defining a plurality of openings 128 therein. For example, a network of wires or threads are interlaced, e.g., woven, to form scaffold 106 having openings 128. In another example, a tube or sheet is laser cut to form openings 128 therein and thus scaffold 106 is integral, i.e., is a single piece and not a plurality of pieces coupled together.

Openings 128 in scaffold 106 are optimized to promote maximum tissue integration in one embodiment. In one embodiment, openings 128 are entirely surrounded by scaffold 106, i.e., are discrete openings. Scaffold 106 is sometimes called a tissue integration scaffold 106.

Scaffold 106 is a metallic material in one of embodiment. For example, scaffold 106 is formed of Nitinol, although is formed from other metallic materials in other embodiments. In another embodiment, scaffold 106 is a polymeric material. Generally, scaffold 106 is formed of a material that supports good tissue integration and incorporation into the vascular wall of the anatomy that scaffolded stent-graft 100 is implanted into.

In one embodiment, scaffold 106 is physically coupled to graft material 104, e.g., using suturing techniques. Accordingly, mechanical advantage provided by integration of scaffold 106 into the vessel wall is directly transferred to scaffolded stent-graft 100 enhancing migration resistance and sealing.

In accordance with this embodiment, scaffold 106 is cylindrical. Scaffold 106 is flexible and of sufficiently low profile that it does not significantly impact the packing density of scaffolded stent-graft 100.

Figure 3A:
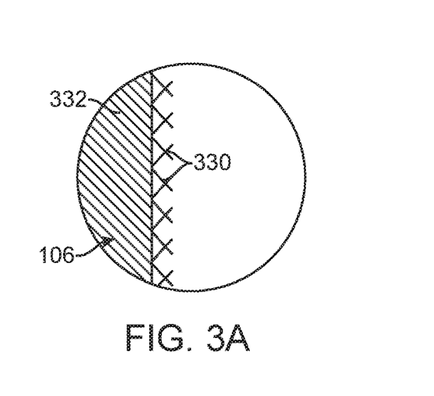
FIG. 3A is an enlarged view of the region III of the scaffolded stent-graft of FIG. 2 in accordance with one embodiment.

FIG. 3A is an enlarged view of the region III of scaffolded stent-graft 100 of FIG. 2 in accordance with one embodiment. Referring to FIG. 3A, in accordance with this embodiment, scaffold 106 includes tissue response enhancing fibers 330 embedded therein. For example, scaffold 106 includes a scaffold body 332, e.g., formed of a mesh of metallic or polymeric materials as described above, and tissue response enhancing fibers 330 embedded within scaffold body 332. Tissue response enhancing fibers 330 are sometimes called fibers of bioactive material.

Tissue response enhancing fibers 330 enhance the tissue response of tissue with scaffolded stent-graft 100. In one embodiment, tissue response enhancing fibers 330 include tissue healing promoting materials, sometimes called scaffolding materials. The tissue healing promoting materials of tissue response enhancing fibers 330 serve to promote the healing process, e.g., the recruitment and proliferation of cells that drive the healing process. Examples of the tissue healing promoting materials of tissue response enhancing fibers 330 include polymer polyglycolic-lactic acid (PGLA), poly(glycerol sebacate) (PGS), animal derived decellularized scaffold, collagen scaffolds, and other tissue healing promoting materials.

In another embodiment, tissue response enhancing fibers 330 include tissue irritant materials that serve to actively drive an inflammatory response that results in a robust fibrocellular response. Examples of the irritant materials of tissue response enhancing fibers 330 include PGLA, polyglycolic acid (PGA), polylactic acid (PLA), silk, bacterial endotoxin, and other irritant materials.

In another embodiment, tissue response enhancing fibers 330 includes an absorbable polymeric material that allows for the elution of bioactive molecules that promote rapid healing and/or promote thrombus formation/maturation. Examples of the bioactive molecules include drugs, peptides, cytokine/chemokine.

Figure 3B:
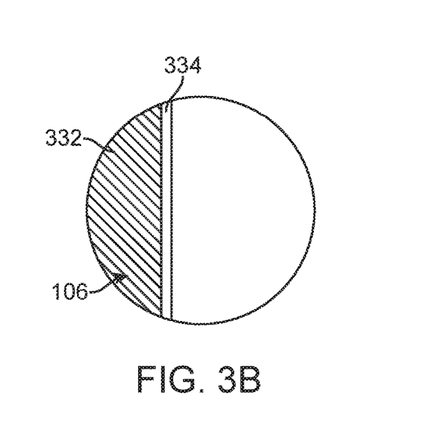
FIG. 3B is an enlarged view of the region III of the scaffolded stent-graft of FIG. 2 in accordance with another embodiment.

FIG. 3B is an enlarged view of the region III of scaffolded stent-graft 100 of FIG. 2 in accordance with another embodiment. Referring to FIG. 3B, in accordance with this embodiment, scaffold 106 includes a tissue response enhancing coating 334. For example, scaffold 106 includes scaffold body 332 and tissue response enhancing coating 334 coated on or impregnated within scaffold body 332. Tissue response enhancing coating 334 enhances the tissue response of tissue with scaffolded stent-graft 100 in a manner similar to tissue response enhancing fibers 330 described above. Tissue response enhancing coating 334 is sometimes called a bioactive material coating.

More particularly, tissue response enhancing coating 334 includes material, e.g., tissue healing promoting materials or irritant materials. In one embodiment, tissue response enhancing coating 334 include tissue healing promoting materials that serve to promote tissue healing, e.g., the recruitment and proliferation of cells that drive the healing process. Examples of the tissue healing promoting materials of tissue response enhancing coating 334 include PGLA, PGS, animal derived decellularized scaffold, collagen scaffolds, and other tissue healing promoting materials.

In another embodiment, tissue response enhancing coating 334 include tissue irritant materials that serve to actively drive an inflammatory response that results in a robust fibrocellular response. Examples of the irritant materials of tissue response enhancing coating 334 include PGLA, PGA, PLA, silk, bacterial endotoxin, and other irritant materials.

In another embodiment, tissue response enhancing coating 334 includes an absorbable polymeric material that allows for the elution of bioactive molecules that promote rapid healing and/or promote thrombus formation/maturation. Examples of the bioactive molecules include drugs, peptides, cytokine/chemokine.

Figure 4:
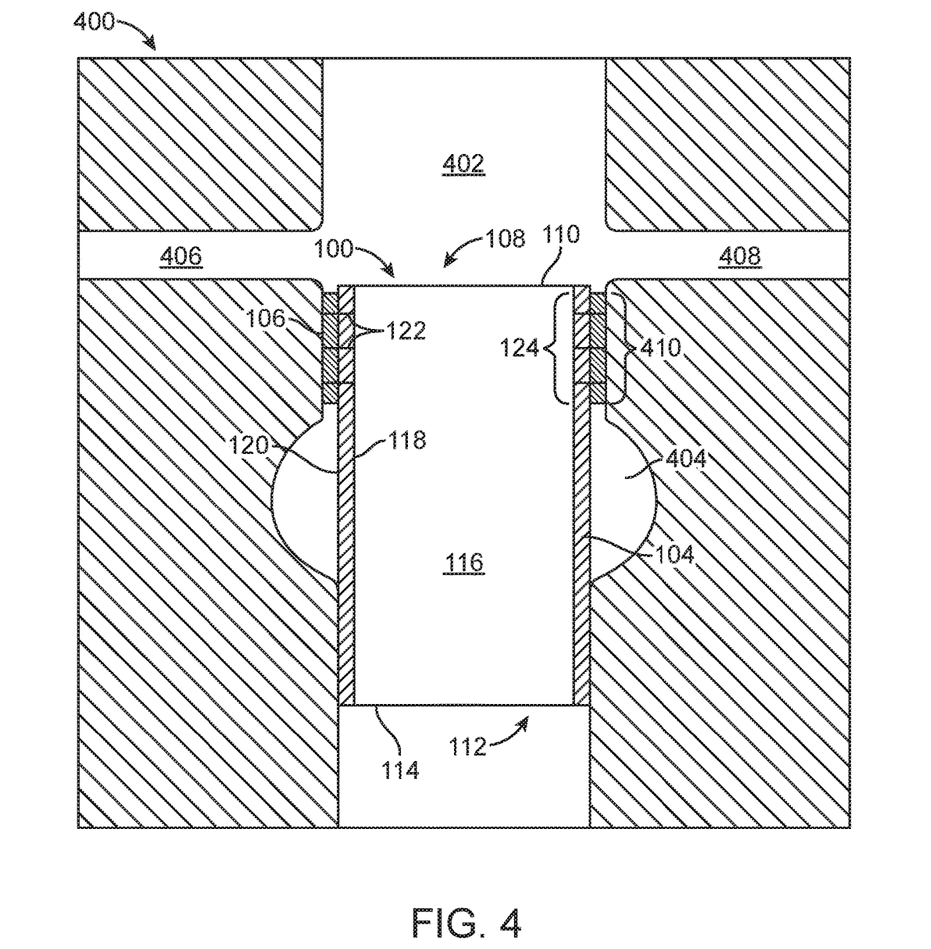
FIG. 4 is a cross-sectional view of a vessel assembly including the scaffolded stent-graft of FIGS. 1 and 2 in accordance with one embodiment.

FIG. 4 is a cross-sectional view of a vessel assembly 400 including scaffolded stent-graft 100 of FIGS. 1 and 2 in accordance with one embodiment. Referring now to FIG. 4, a vessel 402, e.g., the aorta, includes an aneurysm 404. Scaffolded stent-graft 100 is deployed into vessel 402 to exclude aneurysm 404 using any one of a number of techniques well known to those of skill in the art.

Emanating from vessel 402 is a first branch vessel 406 and a second branch vessel 408, sometimes called visceral branches of the abdominal aorta. The location of branch vessels 406, 408 vary from patient to patient. Examples of branch vessels include the renal arteries (RA) and the superior mesenteric artery (SMA).

Scaffolded stent-graft 100 is deployed just distal of branch vessels 406, 408. Scaffold 106, i.e., sealing zone 124, is deployed in the landing zone 410 between branch vessels 406, 408 and aneurysm 404. Over time, tissue from vessel 402 will become integrated with scaffold 106 thus preventing leakage around sealing zone 124 and migration of scaffolded stent-graft 100.

Landing zone 410 is sometimes call a proximal seal zone 410. Although proximal seal zone 410 is discussed, in light of this disclosure, those of skill in the art will understand that generally scaffold 106 can be deployed in any seal zone, e.g., including a distal seal zone.

Once anchored within vessel 402, blood flows through lumen 116 and more generally through scaffolded stent-graft 100 thus excluding aneurysm 404.

Figure 5:
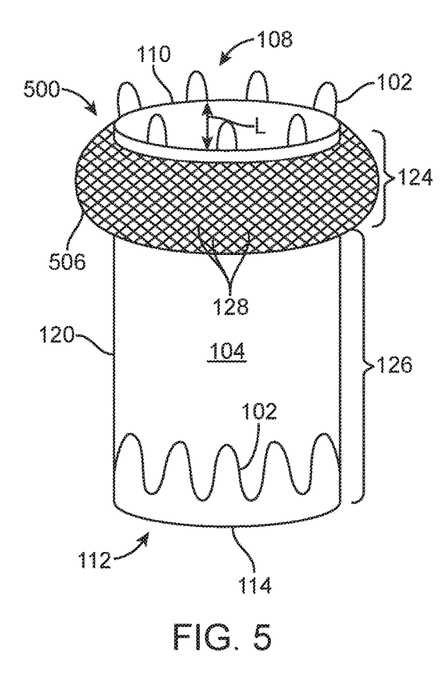
FIG. 5 is a perspective view of a scaffolded stent-graft in accordance with another embodiment.
Figure 6:
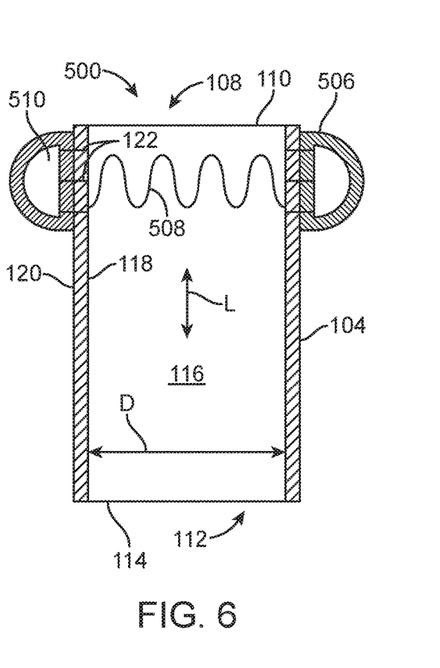
FIG. 6 is a cross-sectional view of the scaffolded stent-graft of FIG. 5 in accordance with one embodiment.

FIG. 5 is a perspective view of a scaffolded stent-graft 500 in accordance with another embodiment. FIG. 6 is a cross-sectional view of scaffolded stent-graft 500 of FIG. 5 in accordance with one embodiment. In FIG. 6, stent rings 102 are not illustrated for clarity of presentation. Scaffolded stent-graft 500 of FIGS. 5, 6 is similar to scaffolded stent-graft 100 of FIGS. 1, 2 and only the significant differences are discussed below.

Referring now to FIGS. 5 and 6 together, scaffolded stent-graft 500 includes graft material 104, a scaffold 506, and a scaffold opposition stent ring 508.

In one embodiment, to enhance tissue integration, scaffold 506 is attached to outer surface 120 of graft material 104 by attachment means 122. In accordance with this embodiment, scaffold 506 is attached to graft material 104 at or adjacent proximal end 110 of graft material 104. The region 124 of graft material 104 which is covered by scaffold 506 is again referred to as seal zone 124 of graft material 104. The region 126 of graft material 104 which is uncovered by scaffold 506 is again referred to as a bare zone 126 of graft material 104.

In accordance with this embodiment, scaffold 506 is formed of the same materials as described above regarding scaffold 106, including metallic materials, polymeric materials, tissue response enhancing fibers 330, scaffold body 332, tissue response enhancing coating 334, and/or combination thereof. The metal to artery ratio of scaffold 506 it is optimized to create stasis of the blood resulting in thrombus formation that helps to promote acute seal. In one embodiment, the metal to artery ratio of scaffold 506 is greater than approximately 30-40% although other metal to artery ratios are used in other embodiments.

In accordance with this embodiment, scaffold 506 is a torus, e.g., shaped like a doughnut. Scaffold 506 is sometimes called a tubular mesh, e.g., includes a thin flexible mesh that will not adversely impact packing density. Scaffold 506 is packed flat in the delivery system to reduce the impact on delivery system packing density but is shape set to take a tubular form, for example, at 37° C. Note that in FIGS. 5 and 6, scaffold 506 is shown in its expanded form and would be collapsed during delivery.

Due to the expansion of scaffold 506 to its tubular form, scaffold 506 applies an inward radial collapsing force on graft material 104. To resist this force and prevent collapse of graft material 104, scaffold opposition stent ring 508, sometimes called a stent graft body spring, is coupled to inner surface 118 of graft material 104 directly opposite scaffold 506. Scaffold opposition stent ring 508 provides an expanding outward radial force greater than the inward radial collapsing force of scaffold 506. Accordingly, scaffold opposition stent ring 508 prevents collapse of graft material 104 from scaffold 506. In one embodiment, due to the inertial properties of scaffold 506 along with blood pressure, scaffold opposition stent ring 508 can be soft, and so thin.

Although a single scaffold opposition stent ring 508 as illustrated, in other embodiments, more than one scaffold opposition stent ring 508 is provided. Further, in yet another embodiment, the inward radial collapsing force on graft material 104 by scaffold 506 is less than the the diastolic pressure, e.g., scaffold 506 has a "soft" construction. In accordance with this embodiment, a scaffold opposition stent ring 508 is unnecessary and not provided. The geometric design is such that scaffolded stent-graft 500 holds its shape in the wake of blood flow even absent scaffold opposition stent ring 508.

In one embodiment, scaffold 506 is filled or coated with a moisture expanding material 510, e.g., a hydrogel. For example, moisture expanding material 510 expands upon making contact with fluid, e.g., blood. The expansion of moisture expanding material 510 further enhances the seal of scaffolded stent-graft 500 within the vessel as described below in reference to FIG. 7.

Figure 7:
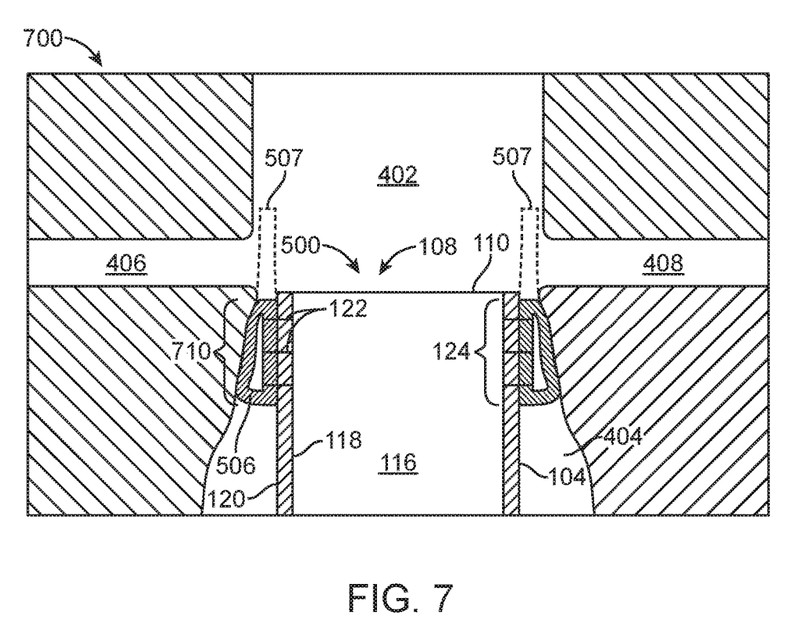
FIG. 7 is a cross-sectional view of a vessel assembly including the scaffolded stent-graft of FIGS. 5 and 6 in accordance with one embodiment.

FIG. 7 is a cross-sectional view of a vessel assembly 700 including scaffolded stent-graft 500 of FIGS. 5 and 6 in accordance with one embodiment. Referring now to FIG. 7, vessel assembly 700 is similar to vessel assembly 400 of FIG. 4 and includes vessel 402, aneurysm 404, and branch vessels 406, 408. Scaffolded stent-graft 500 is deployed into vessel 402 to exclude aneurysm 404 using any one of a number of techniques well known to those of skill in the art.

In accordance with this embodiment, the length of a neck 710 of aneurysm 404 is relatively short. Neck 710 is the area between aneurysm 404 and branch vessels 406, 408, sometimes also called a proximal seal zone 710. Illustratively, the length of neck 710 is 10 mm or less and so is sometimes called a short neck 710. As also illustrated in FIG. 7, the diameter of neck 710 increases as the distal distance from branch vessels 406, 408 increases. Due to the conical shape of neck 710, neck 710 is also sometimes called a conical neck 710.

Although conical short neck 710 is illustrated in FIG. 7 and discussed below, in light of this disclosure, those of skill in the art will understand that scaffolded stent-graft 500 can be deployed in any vessel regardless of the aneurysmal neck length and shape. Further, although proximal seal zone 710 is discussed, in light of this disclosure, those of skill in the art will understand that generally scaffold 506 can be deployed in any seal zone, e.g., including a distal seal zone.

As shown in FIG. 7, scaffold 506 expands to make contact with the wall of neck 710. Scaffold 506 has radial force such that scaffold 506 acts to stabilized scaffolded stent-graft 500 in the void of aneurysm 404. Further, scaffold 506 creates stasis of the blood resulting in thrombus formation that promotes acute seal of scaffolded stent-graft 500 to vessel 402. Scaffold 506 is rapidly integrated into the wall of vessel 402 providing for a permanent enhanced seal and migration resistance. Scaffold 506 is particularly well suited for stabilization in highly angled necks such as neck 710.

Once anchored within vessel 402, blood flows through lumen 116 and more generally through scaffolded stent-graft 500 thus excluding aneurysm 404.

As shown in FIG. 7, in another embodiment, scaffold 506 includes proximal segments 507 that extend proximally past proximal end 110 of graft material 104 and beyond branch vessels 406, 408. In accordance with this embodiment, scaffold 506 is sufficiently porous to not occlude branch vessels 406, 408.

Figure 8:
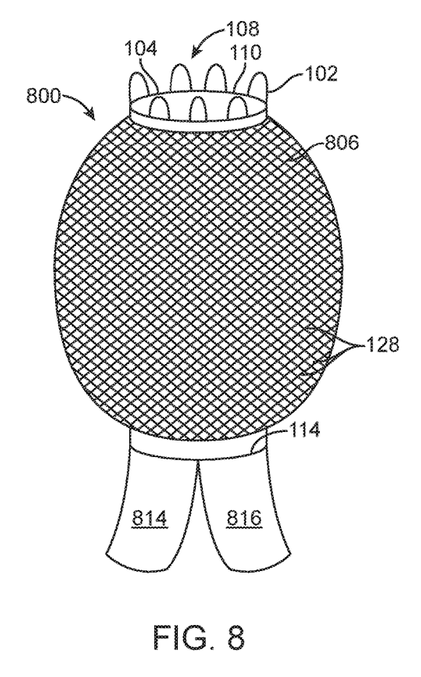
FIG. 8 is a perspective view of a scaffolded stent-graft in accordance with another embodiment.
Figure 9:
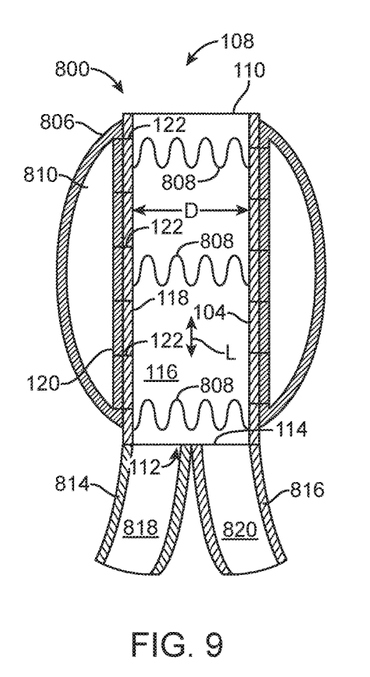
FIG. 9 is a cross-sectional view of the scaffolded stent-graft of FIG. 8 in accordance with one embodiment.

FIG. 8 is a perspective view of a scaffolded stent-graft 800 in accordance with another embodiment. FIG. 9 is a cross-sectional view of scaffolded stent-graft 800 of FIG. 8 in accordance with one embodiment. In FIG. 9, stent rings 102 are not illustrated for clarity of presentation. Scaffolded stent-graft 800 of FIGS. 8, 9 is similar to scaffolded stent-graft 100 of FIGS. 1, 2 and only the significant differences are discussed below.

Referring now to FIGS. 8 and 9 together, scaffolded stent-graft 800 includes graft material 104, a scaffold 806, and scaffold opposition stent rings 808.

In one embodiment, to enhance tissue integration, scaffold 806 is attached to outer surface 120 of graft material 104 by attachment means 122. In accordance with this embodiment, scaffold 806 is attached to graft material 104 along the entire length of graft material 104 and generally between proximal end 110 and distal end 114.

In accordance with this embodiment, scaffold 806 is formed of the same materials as described above regarding scaffold 106, including metallic materials, polymeric materials, tissue response enhancing fibers 330, scaffold body 332, tissue response enhancing coating 334, and/or combination thereof. The metal to artery ratio of scaffold 806 it is optimized to create stasis of the blood in the sac of the aneurysm resulting in thrombus formation. In one embodiment, the metal to artery ratio of scaffold 806 is greater than approximately 30-40% although other metal to artery ratios are used in other embodiments.

In accordance with this embodiment, scaffold 806 is a torus, e.g., shaped like a doughnut. Scaffold 806 is sometimes called a tubular mesh. Scaffold 806 is packed flat, e.g., folded around graft material 104, in the delivery system to reduce the impact on delivery system packing density but is shapes set to take a tubular form, for example, at 37° C. Note that in FIGS. 8 and 9, scaffold 806 is shown in its expanded form and would be collapsed during delivery.

Due to the expansion of scaffold 806 to its tubular form, scaffold 806 applies an inward radial collapsing force on graft material 104. To resist this force and prevent collapse of graft material 104, scaffold opposition stent rings 808, sometimes called stent graft body springs, are coupled to inner surface 118 of graft material 104 directly opposite scaffold 806.

In accordance this embodiment, a plurality of scaffold opposition stent rings 808 are provided along the length of graft material 104. Scaffold opposition stent rings 808 provide an expanding outward radial force greater than the inward radial collapsing force of scaffold 806. Accordingly, scaffold opposition stent rings 808 prevent collapse of graft material 104 from scaffold 806. In one embodiment, due to the inertial properties of scaffold 806 along with blood pressure, scaffold opposition stent rings 808 can be soft, and so thin.

Further, in yet another embodiment, the inward radial collapsing force on graft material 104 by scaffold 806 is less than the the diastolic pressure, e.g., scaffold 806 has a "soft" construction. In accordance with this embodiment, a scaffold opposition stent rings 808 are unnecessary and not provided. The geometric design is such that scaffolded stent-graft 800 holds its shape in the wake of blood flow even absent scaffold opposition stent rings 808.

In one embodiment, scaffold 806 is filled or coated with a moisture expanding material 810, e.g., a hydrogel. For example, moisture expanding material 810 expands upon making contact with fluid, e.g., blood. The expansion of moisture expanding material 810 further enhances the seal of scaffolded stent-graft 800 within the vessel as described below in reference to FIG. 10.

In accordance with this embodiment, scaffolded stent-graft 800 includes extension portions 814, 816. Extension portions 814, 816 extend from distal end 114 of graft material 104. In one embodiment, extension portions 814, 816 are separate pieces, e.g., of graft material, connected to graft material 104. Extension portions 814, 816 are sometime called modular components. In another embodiment, extension portions 814, 816 are integral with graft material 104, e.g., a single piece of graft material is sewn or otherwise manipulated to define extension portions 814, 816.

Extension portions 814, 816 bifurcate main lumen 116 into lumens 818, 820. For example, extension portions 814, 816 are deployed into the iliac arteries. However, in another embodiment, scaffolded stent-graft 800 is formed without extension portions 814, 816. Further, scaffolded stent-grafts 100, 500 as described above include extension portions 814, 816 in other embodiments.

Figure 10:
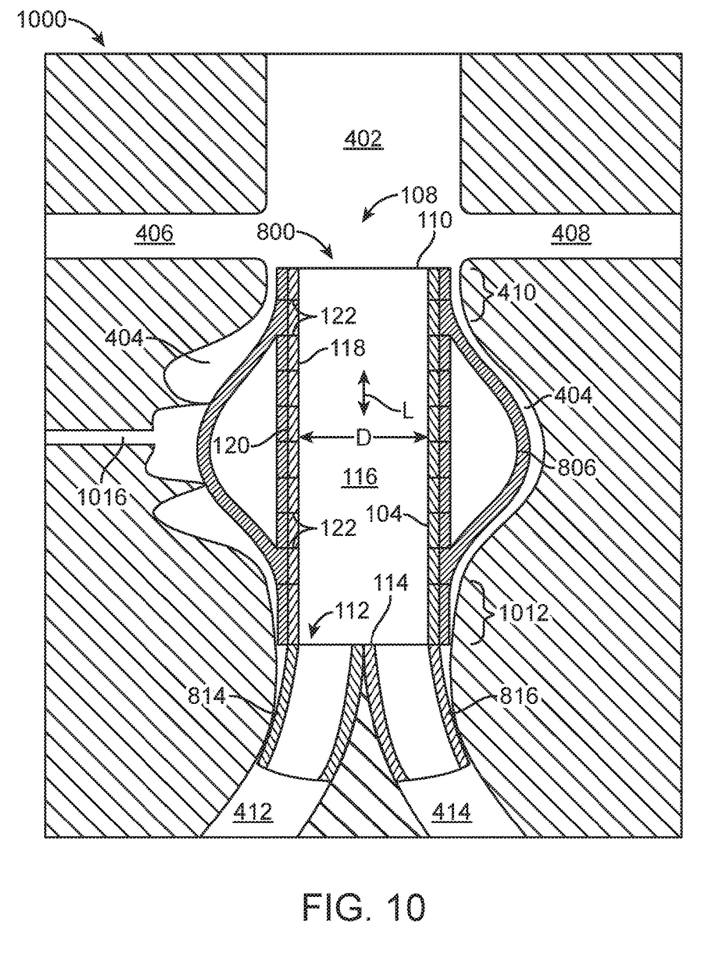
FIG. 10 is a cross-sectional view of a vessel assembly including the scaffolded stent-graft of FIGS. 8 and 9 in accordance with one embodiment.

FIG. 10 is a cross-sectional view of a vessel assembly 1000 including scaffolded stent-graft 800 of FIGS. 8 and 9 in accordance with one embodiment. Referring now to FIG. 10, vessel assembly 1000 is similar to vessel assembly 400 of FIG. 4 and includes vessel 402, aneurysm 404, and branch vessels 406, 408. In accordance with this embodiment, vessel assembly 1000 further includes distal iliac arteries 412, 414. Scaffolded stent-graft 800 is deployed into vessel 402 to exclude aneurysm 404 using any one of a number of techniques well known to those of skill in the art.

In accordance with this embodiment, as shown in FIG. 10, scaffold 806 is deployed to fill the sac of aneurysm 404. By being deployed within aneurysm 404, scaffold 806 anchors scaffolded stent-graft 800 in position. This insures sealing in proximal seal zone 410 and in a distal seal zone 1012 as well as prevents separation of modular components such as extension portions 814, 816.

Further, scaffold 806 creates stasis of the blood in aneurysm 404 resulting in thrombus formation. The formation of the clot within aneurysm 404 minimizes the occurrence of type I and type II endoleaks. Further, scaffold 806 is rapidly integrated into the wall of vessel 402 providing for a permanent enhanced seal and migration resistance.

As illustrated at the left side of scaffolded stent-graft 800, in one embodiment, aneurysm 404 is irregular in shape, e.g., including protrusions, thrombus in the sac of aneurysm 404, and/or including one or more branch vessels 1016 extending thereto. In accordance with this embodiment, contact of scaffold 806 with the actual vessel is unlikely, if not impossible. Scaffold 806 creates stasis of blood and thrombus formation thus occluding branch vessel 1016 preventing filling of aneurysm 404 from branch vessel 1016 and the associated type II endoleaks.

Although branch vessel 1016 is illustrated, branch vessel 1016 is representative of any communication that sets the ground for type II endoleaks. For example, when there is active communication between the inferior mesenteric artery (IMA) and a lumbar artery, the ground is set for a type II endoleak. This communication takes place through a network of cannulae. Scaffold 806 pushes out against the thrombus in the sac and interrupts this path. Once this communication is limited, thrombus forms in the small lumen in the sac thrombus. In one embodiment, scaffold 806 includes thrombogenic material to aid in thrombosis within the sac.

Once anchored within vessel 402, blood flows through lumen 116 and more generally through scaffolded stent-graft 800 thus excluding aneurysm 404. In accordance with this embodiment, extension portions 814, 816 are deployed into iliac arteries 412, 414.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A scaffolded stent-graft comprising:
   a hydrophobic graft material comprising an inner surface and an outer surface, the inner surface defining a lumen within the graft material, the graft material being hostile to tissue ingrowth therein; and
   a scaffold comprising a metallic material mesh comprising openings therein coupled to the graft material at the outer surface, the scaffold configured to promote tissue ingrowth therein, the scaffold comprising a metal to artery ratio optimized to create stasis of blood within the scaffold resulting in thrombus formation, wherein the mesh is in the shape of a torus.

2. The scaffolded stent-graft of claim 1 wherein the graft material comprises a proximal end and a distal end, the scaffold being coupled to the graft material at the proximal end.

3. The scaffolded stent-graft of claim 1 further comprising a moisture expanding material coupled to the scaffold.

4. The scaffolded stent-graft of claim 1 further comprising a stent ring coupled to the graft material at the scaffold, the stent ring configured to provide an expansion force greater than a compression force of the torus.

5. The scaffolded stent-graft of claim 1 wherein the scaffold comprises a tissue healing promoting material coupled to the mesh.

6. The scaffolded stent-graft of claim 1 wherein the scaffold comprises a tissue irritant material coupled to the mesh.

7. The scaffolded stent-graft of claim 1 wherein the metallic material comprises nickel titanium alloy.

8. A scaffolded stent-graft comprising:
   a hydrophobic graft material comprising a proximal end and a distal end, the graft material being hostile to tissue ingrowth therein; and
   a scaffold comprising a metallic material mesh comprising openings therein coupled to an outer surface of the graft material, the scaffold extending substantially between the proximal end and the distal end of the graft material, the scaffold comprising a metal to artery ratio optimized to create stasis of blood within the scaffold resulting in thrombus formation, wherein the mesh is in the shape of a torus.

9. The scaffolded stent-graft of claim 8 wherein the scaffold is configured to fill an aneurysmal sac.

10. The scaffolded stent-graft of claim 8 wherein the mesh is tubular.

11. The scaffolded stent-graft of claim 10 wherein the scaffold comprises a tissue healing promoting material coupled to the mesh.

12. The scaffolded stent-graft of claim 10 wherein the scaffold comprises a tissue irritant material coupled to the mesh.

13. The scaffolded stent-graft of claim 1 wherein the metal to artery ratio of the scaffold is greater than approximately 30-40%.

14. The scaffolded stent-graft of claim 8 wherein the metal to artery ratio of the scaffold is greater than approximately 30-40%.

15. The scaffolded stent-graft of claim 1 wherein the scaffold comprises a thrombogenic material.

16. The scaffolded stent-graft of claim 8 wherein the scaffold comprises a thrombogenic material.

17. The scaffolded stent-graft of claim 1 further comprising stitching attaching the scaffold to the graft material.

18. The scaffolded stent-graft of claim 8 further comprising stitching attaching the scaffold to the graft material.

* * * * *